United States Patent [19]

Simon

[11] 4,163,799

[45] Aug. 7, 1979

[54] PSYCHOSTIMULANT COMPOUNDS

[75] Inventor: Pierre Simon, Sevres, France

[73] Assignee: Union Chimique Continentale U.C.C., Puteaux, France

[21] Appl. No.: 786,485

[22] Filed: Apr. 8, 1977

Related U.S. Application Data

[63] Continuation-in-part of Ser. No. 695,751, Jun. 14, 1976, Pat. No. 4,113,742.

[30] Foreign Application Priority Data

Jun. 13, 1975 [FR] France .............................. 75 18491
Dec. 8, 1976 [FR] France .............................. 76 36942

[51] Int. Cl.$^2$ ............................................ C07D 309/10
[52] U.S. Cl. .................................. 424/317; 260/343.5; 562/468; 562/470
[58] Field of Search ............. 260/343.5, 515 R, 520 B; 560/51; 562/459, 468, 470; 424/317

[56] References Cited

U.S. PATENT DOCUMENTS

| | | | |
|---|---|---|---|
| 2,770,640 | 11/1956 | Journeay | 260/464 |
| 2,904,581 | 9/1959 | Coraor | 260/465.4 |
| 3,278,557 | 10/1966 | Chibnik | 260/343.6 |
| 3,607,885 | 9/1971 | Dombro | 260/343.5 |
| 3,624,144 | 11/1971 | Wendler | 260/521 |
| 3,644,426 | 2/1972 | Dombro | 260/343.5 |
| 3,746,751 | 7/1973 | Noguchi | 260/515 A |
| 4,000,310 | 12/1976 | Simon | 424/279 |

FOREIGN PATENT DOCUMENTS 2314186 1/1977 France .................................. 260/343.5

OTHER PUBLICATIONS

Longeray, Bull. Soc. Chim., France, 1963: 2805-2807.
Baradel, Bull. Soc. Chim., France, 1970: 255-258.
Vigier et al., Chemical Abstracts, vol. 59 (1963) 15, 213.

*Primary Examiner*—Richard Raymond
*Attorney, Agent, or Firm*—Browdy and Neimark

[57] ABSTRACT

Tetrahydro-α-pyrones and their intermediate salts of 5-hydroxy-2,3-diphenyl hexanoic acid have psychostimulant activity. A process for the preparation of these compounds comprises preparing the alkyl ester of a 5-oxo alkanoic acid from a 4-oxo alkane carbonitrile, obtained in a first stage by the action of benzyl cyanide on the corresponding alkenone, and then saponifying the obtained ester, followed by hydrogenation to form the 5-hydroxy-2,3-diphenyl hexanoic acid salt, followed if desired by cyclization to form the tetrahydro-α-pyrone.

7 Claims, No Drawings

PSYCHOSTIMULANT COMPOUNDS

FIELD OF THE INVENTION

The present invention relates to new analeptic drugs, more particularly to psychostimulants, and to a method of preparing them. This is a CIP of copending application Ser. No. 695,751, filed June 14, 1976, now U.S. Pat. No. 4,113,742, which is incorporated herein by reference.

BACKGROUND OF THE INVENTION

Examples of preparation of tetrahydrogenated α-pyrones have already been given in literature. Mention may be made for example of the preparation of 4,4,6-trimethyl 3-phenyl 2-tetrahydropyrone (R. LONGERAY and J. DREUX in Bull. Soc. Chim. Fr. 1963, 2805) or the preparation of 6-methyl 3,4-diphenyl 3,4,5,6-tetrahydro-2-pyrone (A. M. BARADEL, R. LONGERAY and J. DREUX, Bull. Soc. Chim. Fr. 1970, 255). The process described in these publications are long and complicated and further have the disadvantage of a poor overall yield, hardly exceeding 1%, which in practice forbids the manufacture of these derivatives on the industrial scale, by reason both of the difficulties of preparation and of the lack of economic profitability.

SUMMARY OF THE INVENTION

The present invention relates to a new process for the preparation of α-pyrones. It relates more particularly to a new process for the preparation of tetrahydro-α-pyrones which correspond to the following general formula I:

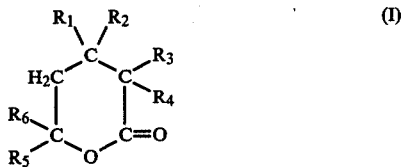

wherein:

$R_1$, $R_2$, $R_3$, $R_4$, $R_5$, $R_6$, which can be identical or different, represent a hydrogen atom or substituted or unsubstituted alkyl, aryl or aralkyl groups, and more particularly wherein $R_3$ is phenyl and $R_4$ and $R_5$ are hydrogen.

The present invention also relates to novel tetrahydro-α-pyrones of the above formula having psychostimulant activity, and also to novel intermediates thereof having analeptic, and particularly psychostimulant activity, obtained during the course of preparing said pyrones, particularly obtained during the course of preparing 6-methyl-3,4-diphenyl-3,4,5,6-tetrahydro-2-pyrone.

The present invention also relates to novel pharmaceutical compositions and to methods of administration of the novel psychostimulant compounds, particularly pharmaceutically effective salts of 5-hydroxy-2,3-diphenyl hexanoic acid.

The products of the present invention are found to have effective psychostimulant activity; see, for example U.S. Pat. No. 4,000,310. Furthermore, the process of synthesizing such products is simple, economical and effective.

DETAILED DESCRIPTION OF EMBODIMENTS

Consequently, an object of the present invention is to provide a new process for the preparation of tetrahydro-α-pyrones which process responds better to the requirements of practice than the processes described in the prior art, especially in that it gives rise to very satisfactory yields which, added to a substantial simplification of the stages of the process, permit its utilization on the industrial scale, with good conditions of economic profitability.

The present invention has for another object a new process for the preparation of tetrahydro-α-pyrones, characterized in that the alkyl ester of a 5-oxo alkanoic acid is prepared from a 4-oxo alkane carbonitrile obtained in the course of a first stage of the process by the action of benzyl cyanide upon the corresponding alkenone, the obtained ester being saponified in an appropriate medium, hydrogenated and cyclized in the course of a third stage of the process, in order to arrive at the desired tetrahydro-α-pyrone.

Alternatively, the process may be cut short after the hydrogenation step and before the cyclization step (both referred to above as part of the third state) and the 5-hydroxy-2,3-diphenyl hexanoic acid salt isolated and purified.

In accordance with a preferred embodiment of the process which forms an object of the present invention, the reaction of the benzyl cyanide upon the alkenones for the obtaining of 4-oxo alkane carbonitrile, which constitutes the first stage of the process, is carried out in a solvent comprising an ethanol-hexane mixture and in the presence of a catalyst of KOH.

According to another preferred embodiment of the process forming the object of the present invention, the preparation of the ethyl ester of 5-oxo alkanoic acid from the corresponding 4-oxo alkane carbonitrile by reaction with a suitable alkanol, which constitutes the second stage of the process, takes place in the presence of an acid.

According to an advantageous way of execution of the third stage of the process forming an object of the present invention, the hydrogenation of the ester is effected before its saponification.

According to another advantageous way of execution of the third stage of the process according to the present invention, the saponification and the hydrogenation are carried out simultaneously in the hydrogenation bomb.

According to yet a further advantageous way of execution of the third stage of the process according to the present invention, when the saponification and/or the hydrogenation take place in alcoholic medium, the latter is eliminated by distillation, followed by the cyclization if one wishes to produce the pyrone.

According to an advantageous embodiment of the process according to the present invention, the hydrogenation catalyst is nickel obtained from Raney alloy.

According to one of its particularly advantageous embodiments, the hydrogenation effected in the course of the third stage of the process according to the present invention is carried out under pressure.

According to another preferred embodiment of the process according to the present invention, the cyclization effected in the course of the third stage is carried out in the presence of an acid.

According to yet another particularly advantageous embodiment of the process according to the present invention, the intermediate products obtained respectively in the course of the first and second stages of the process are purified by recrystallization in absolute alcohol containing 0 to 2% of $H_2SO_4$.

Apart from the above features, the invention includes still further features which appear from the following description.

The present invention relates more particularly to the process for the preparation of α-pyrones in accordance with the above features, and to the means adapted for carrying out this process, also the overall processes and manufacturing chains in which the processes according to the present invention are included.

The present invention also relates to such a method characterized in that, during the first stage, 4-oxo-1,2-diphenyl-pentane carbonitrile is prepared by causing benzyl cyanide to act on 4-phenyl-3-butene-2-one; in that, during the second stage, the ethyl ester of 5-oxo-2,3-diphenyl hexanoic acid is prepared; and in that, during the third stage, just before the cyclization which would produce the desired α-pyrones, a pharmaceutically effective salt, e.g. the sodium salt, of 5-hydroxy-2,3-diphenyl hexanoic acid is produced by saponification and hydrogenation from the ethyl ester of 5-oxo-2,3-diphenyl hexanoic acid according to the following reaction:

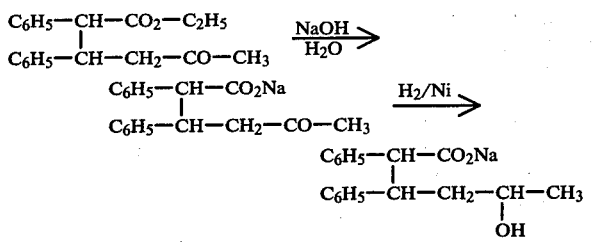

Surprisingly enough, the applicant has discovered that this intermediate in the preparation of α-pyrones, constituted by a pharmaceutically effective salt, such as an alkali or alkaline earth metal salt, of 5-hydroxy-2,3-diphenyl hexanoic acid, after isolation and purification, possesses remarkable therapeutic properties, in particular psychoanaleptic properties with a stimulating effect and increase in wakefulness, which properties permit the therapeutic utilization of this substance in cases of apathy, asthenia, memory problems, difficulties in focusing the attention, and difficulties of concentration in general, as well as to correct conditions of sedation caused by the administration of antielleptics, tranquilizers, neuroleptics, etc.

The present invention also has the purpose of simplifying the above-described method of preparation of alkali salts of 5-hydroxy-2,3-diphenyl hexanoic acid.

The present invention has for its subject a new drug with powerful psychostimulating properties, characterized by being composed of an alkali or other pharmaceutically effective salt of 5-hydroxy-2,3-diphenyl hexanoic acid:

 threo isomer

Me being preferably an alkali metal, which alkali salt may be associated with conventional pharmaceutically compatible vehicles and/or excipients such that it can be administered orally, parenterally, or rectally.

The present invention also has as its subject a method for preparing alkaline salts of 5-hydroxy-2,3-diphenyl hexanoic acid characterized in that, during the first stage of the process, 4-oxo-1,2-diphenyl pentane carbonitrile is prepared by causing benzyl cyanide to act on 4-phenyl-3-butene-2-one in a solvent preferably comprising an ethanolhexane mixture and in the presence of a KOH catalyst; and, in that, during the second stage, the ethyl ether of 5-oxo-2,3-diphenyl hexanoic acid is prepared in the presence of an acid; and in that, during the third stage, the ester so formed is saponified, then the salt obtained is converted by hydrogenation into a salt of 5-hydroxy-2,3-diphenyl hexanoic acid; and in that, during a fourth stage, the salt of the 5-hydroxy-2,3-diphenyl hexanoic acid is separated by evaporation, filtration, and double crystallization.

According to a particularly advantageous embodiment of the process subject to the present invention, the carbonitrile

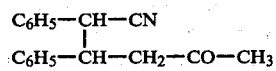

is directly hydrolized by an alkali into an alkaline salt of 5-oxo-2,3-diphenyl hexanoic acid.

The present invention particularly encompasses the new drugs composed of or including the alkaline salt of 5-hydroxy-2,3-diphenyl hexanoic acid according to the provisions hereinabove as well as the various forms of administration in which they are prepared.

The invention will be better understood with the aid of the following supplementary description which refers to examples of carrying out of the process according to the present invention and preparation of the drugs according to the present invention, and to the results of pharmacological and pharmacodynamic tests which show the efficiency of new drugs of the present invention as psychostimulantes. It must however by clearly understood that the examples described set forth are given solely by way of illustration, but in no way constitute a limitation thereof.

EXAMPLE 1

Preparation of 6-methyl 3,4-diphenyl 3,4,5,6-tetrahydro 2-pyrone.

1st stage

Preparation of the 1,2-diphenyl 4-oxo pentane carbonitrile:

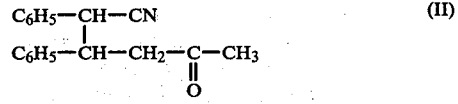

Seventy-three grams (0.5 mol) of 4-phenyl 3-butene 2-one trans are dissolved in 60 g (0.51 mol) of benzyl cyanide. 200 ml of the mixtures of hexane and absolute alcohol (70:30) are added. The solution is agitated and cooled in a cooling bath at about −5° C. Then the catalyst is added: 20 ml of 2 N ethanol KOH. The addition must be slow (about 1 hour) and the temperature must not exceed 0° C.

In the reaction vessel a crystallization is observed which develops with time. Four hours after the beginning of the addition, the reaction vessel is placed in the refrigerator for the night. At the end of this time the content of the vessel, which is partly set in a lump, is filtered. The crystals are washed twice with 100 ml then once with 200 ml of cold hexane, then twice with 100 ml of cold methanol in order to eliminate the potash. The yield is of the order of 90l %.

The CVP analysis indicates a content of 98% of threo product and 2% of erythro product. There is no more starting product.

| Analysis C$_{18}$H$_{17}$ON. | C | H | N |
|---|---|---|---|
| Calculated % | 82.10 | 6.51 | 5.32 |
| Found % | 82.04 | 6.53 | 5.39 |

Recrystallization from a solution of absolute alcohol containing 1% by weight of sulphuric acid gives a product having a content of 100% of threo isomer.
Yield 80%
Melting point 100° C.

2nd Stage
Preparation of the ethyl ester of 2,3-diphenyl 5-oxo 2-hexanoic acid:

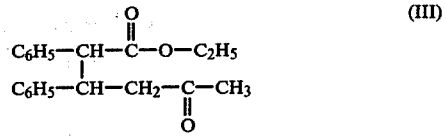

(III)

Thirty grams of 1-2 diphenyl 4-oxo pentane carbonitrile obtained in the course of the first stage are dissolved in the hot state in 270 ml of alcohol at 95° GL. Then 90 ml of concentrated sulphuric acid are added. The reaction mixture is heated under reflux for 6 hours. After cooling it is extracted at least 4 times with 200-100-100-100 ml of CH$_2$Cl$_2$— ether (50:50), until almost complete decolorization of the aqueous phase has occured.

The recovered rich organic phase is washed twice with 100 ml of a 10% solution of Na$_2$CO$_3$, then 3 times with 100 ml of brine and then dried over sodium sulphate.

After evaporation of the solvents, the product is distilled in vacuo: it passes at 166°–167° C. at 0.6 mm of mercury.

Yield of second stage: 80% approximately—melting point: 95° C.

| Analysis C$_{20}$H$_{22}$O$_3$ | C | H |
|---|---|---|
| Calculated % | 77.39 | 7.14 |
| Found % | 77.14 | 7.12 |

3rd Stage
Preparation of 6-methyl 3,4-diphenyl 3,4,5,6-tetrahydro 2-pyrone. Twenty grams (0.064 mol) of ethyl ester of 2,3-diphenyl 5-one hexanoic acid are placed in suspension in 20 ml of 10 N soda and 130 ml of water and placed in an hydrogenation bomb. Then neutral nickel is added with 50 ml of water. The nickel is obtained from 8 g. of Raney alloy. Neutral nickel is used in order to know the exact quantity of soda utilized.

The procedure of saponification and hydrogenation lasts 12 hours at 100° C. under 10 bars. The unsaponifiable substances are extracted with ether (100 ml), the ethyl alcohol is eliminated by evaporation. At this stage the product comprises the sodium salt of 5-hydroxy-2,3-diphenyl hexanoic acid.

After filtration of the nickel, the alkaline solution is acidfied with 20 ml of concentrated HCl and brought to boiling during 1 hour. After cooling and saturation with NaCl, extraction is effected 3 times with 200-100-100 ml of ether-CH$_2$Cl$_2$ mixture (50—50). The organic phase is washed with twice 100 ml of a saturated solution of NaHCO$_3$, 3 times with 100 ml of brine and dried over sodium sulphate. After evaporation of the solvent, the solid white residue is taken up hot in 80 ml of absolute alcohol, then hot filtered.

Crystallization gives very white crystals; 12.3 g.
Yield: 73% Melting point: 135° C.

A single recrystallization brings the melting point to 140° C., which melting point is then constant. Recrystallization yield 80%. Yield of the third stage in pure product=73×80:58%.

| Analysis C$_{18}$H$_{18}$O$_2$ | C | H |
|---|---|---|
| Calculated % | 81.17 | 6.81 |
| Found % | 81.19 | 6.92 |

Spectroscopic Analyses

The infra-red spectra have been obtained on a Perkin-Elmer 257 apparatus (KBr Pastille).

The RMN spectra were recorded at 60 MHz on a Varian A-60 spectrometer

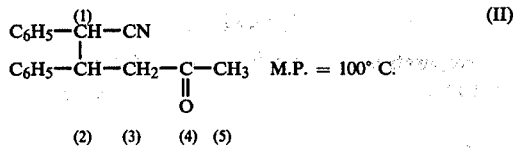

(II)

IR:νC≡N:2220 cm$^{-1}$:νC=O:1705 cm$^{-1}$
RMN:δ=7.17 signal for 10 protons (phenyl) (CDCl$_3$)
δ=4.10 doublet for H$_{(1)}$ J$_{H(1)}$ H$_{(2)}$=7 Hz
δ=3.72 multiplet for H$_{(2)}$
δ=3.01 multiplet for 2 H$_{(3)}$
δ=2.0 singlet for CH$_{3(5)}$

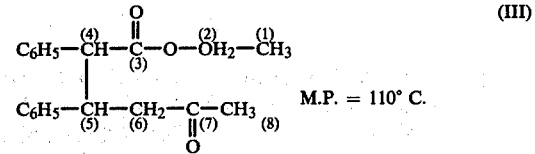

(III)

M.P. = 110° C.

IR:νC=O very great between 1700 and 1740 cm$^{-1}$;
>C=O and

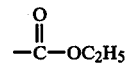

RMN:δ=7.30 signal for 10 aromatic protons (CDCl$_3$)
δ=3.80 solid for 4 protons
δ=2.45 solid for 2 protons
δ=1.69 singlet for CH$_3$ (8)
δ=0.85 triplet for CH$_{3(1)}$J$_{CH_3,CH_2}$=7 Hz

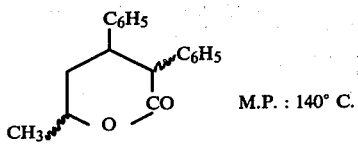

M.P. : 140° C.

IR:νC=O:1725 cm$^{-1}$

RMN:2 spectra, in deuteriated acetone and in deuteriated chloroform:

In deuteriated acetone:

$\delta = 7.10$ signal for 10 aromatic protons, $\delta = 4.85$ solid poorly resolved for $H_{(6)}$ $\delta = 4.20$ doublet for $H_{(3)} J_{H,H} = 11.1$ Hz for one isomer $\delta = 3.90$ doublet for $H_{(3)} J_{H,H} = 11.6$ Hz for the other isomer $\delta = 3.50$ solid poorly resolved for $H_{(4)}$ $\delta = 2.18$ superposed triplets (2 isomers) for $CH_{2(5)}$ coupled to $H_{(4)}$ and $H_{(6)}$ $\delta = 1.42$ doublet for $CH_{3(6)}$ one isomer $J_{CH_3,H_6} = 6$ Hz $\delta = 1.40$ doublet for $CH_{3(6)}$ the other isomer $J_{CH_3,H_6} = 6$ Hz According to the preparation one obtains 35–45% for the minority diastereoisomer. The quantity regulation of the two isomers can be effected with the doublets $\delta = 4.20$ and 3.90. The couplings $H_{(3)} H_{(4)} = 11$ indicate a transaxial position, which permits of attributing the threo configuration to the products II and III.

The spectrum is deuteriated chloroform shows only one doublet for $CH_{3(6)} (\delta = 1.49)$ and a single doublet for $H_{(3)} (\delta = 3.85)$.

EXAMPLE 2

Preparation of 3,4,6-triphenyl 3,4,5,6-tetrahydro 2-pyrone.

1st stage :

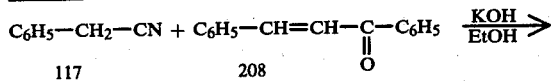

Yield = 95%

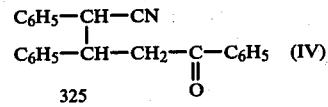

20.8 g (0.1 mol) of chalcone (1,3-diphenyl 1-propenone) are dissolved hot in 12.0 g (0.102 mol) of benzyl cyanide. 60 ml of hexane-absolute alcohol mixture (20-80) are added; the reaction medium is cooled to 0° C. in an ice-salt mixture. The catalyst (8 ml of 2 N ethanol KOH) is then added slowly. Crystallisation intervenes very quickly in the vessel, about 1 hour after the beginning of pouring which lasts ¾ of an hour. The vessel is then placed in the refrigerator for the night.

The crystals contained in the vessel are filtered and washed with 3 times 30 ml of cold hexane then once with 30 ml of cold methanol.

Mass = 30.8 g.

Yield:95%

M.P.:112° C.

CVP analysis shows only one single peak (no more starting product).

Two recrystallisations from absolute alcohol (the first in the presence of 1% $H_2SO_4$) bring the melting point to 116° C., which melting point then remains constant (no difference in IR).

| Analysis $C_{23}H_{19}ON$ | C | H | N |
|---|---|---|---|
| Calculated % | 84.89 | 5.89 | 4.30 |
| Found % | 84.98 | 5.94 | 4.39 |

2nd Stage

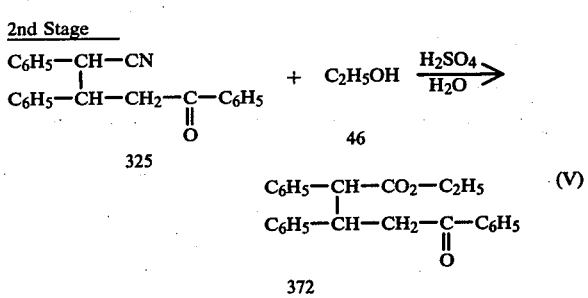

Yield of crude product:80%; Yield of pure product:65%

50 g (0.134 mol) of 1,2,4-triphenyl 4-oxo butane carbonitrile are dissolved hot in 500 ml of alcohol at 95° GL. After dissolving, 200 ml of concentrated sulphuric acid are poured.

The solution, under vigorous mechanical agitation, is heated under reflux for 7 hours. After 3 hours, crystals appear in the vessel and the solution thickens. Cooling accentuates the setting. In order to dissolve the whole, 150 ml of $CH_2Cl_2$ are added and heating is effected under reflux; nothing re-precipitates by cooling. The mixture is poured into 300 ml of brine. The decanted aqueous phase is again extracted with 3 times 100 ml of ether-$CH_2Cl_2$ mixture (50—50). The collected organic phases are washed with 100 ml of a 10% solution of $Na_2CO_3$ then with 3 times 200 ml of brine and dried over sodium sulphate. After evaporation the solid residue is taken up with 300 ml of alcohol, hotfiltered and crystallised.

After filtration and drying, 45.9 g. of light white product are recovered, M.P.: 147° C., yield: 80%

Yield of the recrystallisation: 80%.

M.P.: 150° C. (absolute alcohol).

| Analysis $C_{25}H_{24}O_3$ | C | H |
|---|---|---|
| Calculated % | 80.62 | 6.50 |
| Found % | 80.46 | 6.40 |

3rd stage

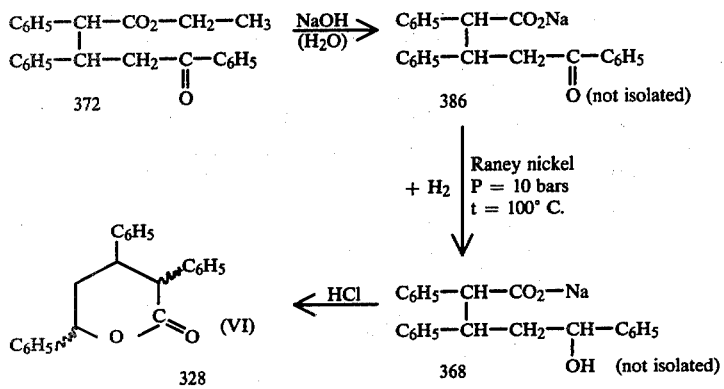

Crude yield: 82%
Yield of purified product: 62%

18 g (0.048 mol) of ethyl ester of 2,3,5-triphenyl 5-oxopentanoic acid (pure in CVP) are saponified by heating under reflux for 4 hours in a sodium hydroalcoholic solution (18 ml of 10 N NaOH, 100 ml of alcohol at 95° GL and 50 ccs. of water). Then the hot solution is filtered in the hydrogenation bomb. The neutral nickel prepared from 5 g. of Raney alloy with 50 ml of water is added.

The hydrogenation lasts 14 hours, p: 10 bars, t: 100° C. After filtration of the nickel, 100 ml of water are added to the filtrate and the ethyl alcohol is eliminated by distillation. After cooling, acidification is effected with agitation with 18 ml of concentrated HCl, then heating is effected under reflux for 1 hour, still with agitation. After cooling, the product is filtered over a Buchner funnel. 13.0 g. of yellowish crystals are collected, MP=198° C.; Yield=82%.

Re-crystallisation in the benzene-butanone mixture (50—50) MP=205° C.

| Analysis C$_{23}$H$_{20}$O$_2$ | C | H |
|---|---|---|
| Calculated % | 84.12 | 6.24 |
| Found % | 83.74 | 6.40 |

Spectroscopic Analysis
(KBr Pastille for the I.R.)

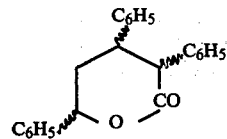   IV

M.P.: 116° C. (absolute alcohol) (IV)
IR: $1/\nu C\equiv N$: 2205 cm$^{-1}$; $\nu C\!=\!\!O$: 1670 cm$^{-1}$
RMN: in deuteriated chloroform.
$\delta=8$ to 7 ppm spread solid for 15 aromatic protons
$\delta=4.5$ ppm doublet for 1H in (1); $J_{H(1)H(2)}=5$ Hz
$\delta=$ from 4 to 3.5 ppm solid poorly resolved for 1H in (2) and 2H in (3).

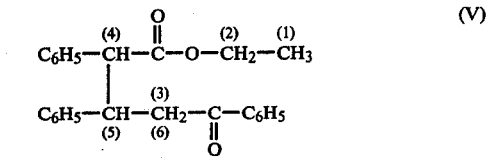

MP: 150° C. (absolute alcohol)
IR: 2 bands C=O, CO in $\alpha$ of a phenyl at 1670 cm$^{-1}$; CO ester at 1710 cm$^{-1}$
RMN: $\delta=7.30$ signal for 15 aromatic protons
(CDCl$_3$) $\delta=3.82$ solid for 4 protons
$\delta=3.07$ solid for 2 protons
$\delta=0.89$ one triplet for CH$_{3(1)}$ $J_{CH_3,CH_2}=7$ Hz

   VI

MP=205° C. (butanone-benzene 50—50)
IR(KBr): $\delta$C=O: 1700 cm$^{-1}$

EXAMPLE 3

Preparation of 4,4,6-Trimethyl 3-phenyl, 2-tetrahydropyrone

1st stage

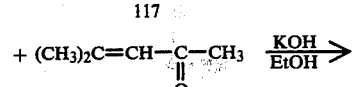   (VII)

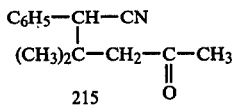

Yield: 87%

29.4 g (0.30 mol) of 4-methyl 3-pentene 2-one are dissolved in 36 g (0.31 mol) of benzyl cyanide. 80 ml of the mixture of hexane and absolute alcohol (80-20) are added. The stirred solution is cooled to 0° C. in an ice-salt mixture. When the temperature is of the order of −2° C., the ethyl potash is added, firstly until neutralisation of the acid impurities contained in the mesityl oxide (checked with pH paper), then 5 ml. to catalyse the reaction. One hour after the end of pouring a beginning of crystallisation is noted. Two hours later the vessel is placed in the refrigerator.

The content of the vessel, completely solidified, is filtered over fritted glass. The crystals are washed with twice 100 ccs. of cold hexane then 100 ml of cold methanol. MP=90° C., Yield=87%.

MP=93° C. (ethyl alcohol); the first crystallisation takes place in the presence of traces of sulphuric acid.

2nd stage $$\underset{215}{\underset{(CH_3)_2C-CH_2-\underset{\underset{O}{\|}}{C}-CH_3}{C_6H_5-CH-CN}} + C_2H_5OH \xrightarrow[H_2O]{H_2SO_4} \underset{262}{\underset{(CH_3)_2C-CH_2-\underset{\underset{O}{\|}}{C}-CH_3}{C_6H_5CH-CO_2-C_2H_5}} \quad (VIII)$$

Yield=70%

25 g. (0.116 mol) of 2,2-dimethyl 4-oxo 1-phenyl pentane carbonitrile are dissolved hot in 240 ml of alcohol at 95° GL. Then 90 ml of concentrated $H_2SO_4$ are poured and heating is effected under reflux for 6 hours.

After cooling the solution is diluted with 200 ml of brine, then extracted with 200-100-100-100 ml of $CH_2Cl_2$-ether mixture (50—50).

The recovered organic phase is washed with 100 ml of a 10% solution of $Na_2CO_3$ then with three times 100 ml of brine and finally dried over sodium sulphate.

After evaporation of the solvents, the product is distilled in vacuo. It passes at 145°-150° C. (p=1.5 mm of Hg). Yield: 70%. Colourless slightly viscous liquid product.

| Analysis: $C_{16}H_{22}O_3$ | C | H |
|---|---|---|
| Calculated % | 73.25 | 8.45 |
| Found % | 73.28 | 8.22 |

3rd stage $$\underset{262}{\underset{(CH_3)_2C-CH_2-\underset{\underset{O}{\|}}{C}-CH_3}{C_6H_5-CH-CO_2-C_2H_5}} \xrightarrow[40]{+NaOH} \underset{256}{\underset{(CH_3)_2C-CH_2-\underset{\underset{O}{\|}}{C}-CH_3}{C_6H_5-CH-CO_2Na}}$$

(not isolated)

$$+H_2 \left| \begin{array}{l} \text{Raney nickel} \\ p=20 \text{ bars} \\ t=100° \text{ C.} \end{array} \right.$$

(IX) [structure with CH3, CH3, C6H5, CH3, O, =O, labeled 218]

$\xleftarrow{HCl}$ $\underset{258 \quad OH}{\underset{(CH_3)_2C-CH_2CH-CH_3}{C_6H_5-CH-CO_2Na}}$ (not isolated)

Crude yield: 50%
Yield of purified product: 38%

15 g. (0.057 mol) of ethyl ester of 3,3-dimethyl 5-oxo 2-phenyl hexanoic acid are saponified for 3 hours by heating under reflux in a solution containing 20 ml of 10 N soda, 50 ml of alcohol at 95° GL and 50 ml of water. The solution is filtered and placed in the hydrogenation bomb and the neutral Raney nickel is added (prepared from 6 g. of Raney alloy) with 50 ml of water.

Hydrogenation lasts 14 hours at 100° C. (under a pressure of 10 bars).

After filtration of the nickel and addition of 200 ml of water, the ethyl alcohol is evaporated then acidification is effected with 20 ml of conentrated HCl and heating is effected for 1 hour under reflux.

After cooling and saturation by NaCl, extraction is effected with three times 100 ml of ether $CH_2Cl_2$ mixture (50—50).

The recovered organic phases are washed with 100 ml of an 8% solution of $NaHCO_3$, twice 100 ml of brine, then dried over sodium sulphate.

After evaporation of the solvents, the white residue is re-dissolved hot in 20 ml of hexane-absolute alcohol mixture (60-40).

Crystallisation gives very white crystals: 6.4 g. Yield: 50% MP: 77° C. (hexane-absolute alcohol).

A recrystallisation from 25 ml of hexane-absolute alcohol mixture (20-30) brings the melting point to 80° C. Yield: 75% Pure product in CVP. Recrystallisation to constant melting point MP=81° C.

| Analysis: $C_{14}H_{18}O_2$ | C | H |
|---|---|---|
| Calc. % | 77.03 | 8.31 |
| Found % | 76.82 | 8.36 |

Spectroscopic Analysis (1) VII $$\underset{(CH_3)_2C-CH_2-\underset{\underset{O}{\|}}{C}-CH_3}{C_6H_5-CH-CN}$$

(2) (3) (4)

MP: 93° C. (absolute alcohol)
IR: $\nu C\equiv N$. 2210 $cm^{-1}$; $\nu C=O$: 1690 $cm^{-1}$
RMN: (solvent: $CDCl_3$):

$\delta=7.28$ one signal for five aromatic protons $\delta=4.47$ one singlet for $H_{(1)}$
$\delta=2.67$ and 2.25 two doublets for $2H_{(3)}$, $J_{H,H}=17$ Hz
$\delta=2.10$ one singlet for $3H_{(4)}$
$\delta=1.05$ and 1.20 two singlets for $6H_{(2)}$ This spectrum is in accordance with the asymmetry of the molecule.

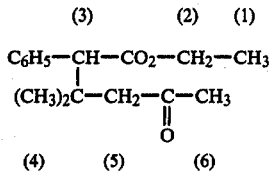

b.p.$_{0.3}$: 116°–118° C. (VIII)
IR: $\nu C\!=\!O$ between 1710 and 1740 cm$^{-1}$
RMN: (CDCl$_3$):
$\delta = 7.25$ one signal for five aromatic protons
$\delta = 4.10$ and 4.06 two quadruplets for 2H$_{(2)}$ $J_{H,H}=5.5$ Hz and $J_{H,H}=5.5$ Hz
$\delta = 3.95$ one singlet for H$_{(3)}$
$\delta = 2.73$ and 2.23 two doublets for 2H$_{(5)}$, $J_{H,H}=16$ Hz
$\delta = 2.02$ one singlet for 3H$_{(6)}$
$\delta = 1.18$ one solid for 6H$_{(4)}$ and 3H$_{(1)}$
This spectrum is in accordance with the asymmetry of the molecule.

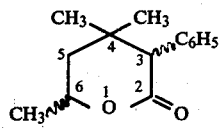

MP: 81° C. (hexane-absolute alcohol 70–30)
IR: $\nu C\!=\!O$: 1700 cm$^{-1}$
RMN: spectrum in deuteriated acetone
$\delta = 7.25$ signal for 5 aromatic protons
$\delta = 4.75$ solid poorly resolved for H (6)
$\delta = 3.75$ and 3.61 two singlets for H (3), each corresponding to a diasterioisomer of 5.
$\delta = 1.75$ one solid for the methylene in 5.
$\delta = 1.4$ one doublet for the methyl in 6 of a diasterioisomer ($J_{CH_3,H}=6$ Hz)
$\delta = 1.37$ one doublet for the methyl in 6 of the other diasterioisomer ($J_{CH_3,H}=6$ Hz)
$\delta = 1.11$ and 0.8 two singlets for the methyls in 4 of one of the diasterioisomers
$\delta = 1.0$ and 0.91 two singlets for the methyls in four of the other isomer. p The signals divided by the presence of two diasterioisomers are in an approximate ratio of 55-45.

EXAMPLE 4

Example of Preparation of the Sodium Salt of 5-Hydroxy-2,3-Diphenyl-Hexanoic Acid

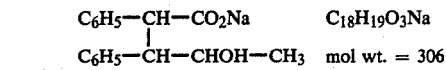

Stage one

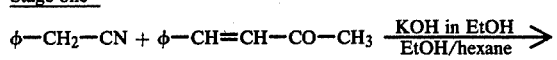

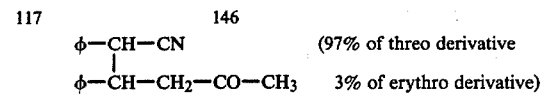

Two hundred and sixty three gms (1.8 mol) of trans-4-phenyl-3-butene-2-one are dissolved in 211 g of benzyl cyanide (1.8 mol). Seven hundred, twenty cc of an absolute hexane-alcohol mixture (70-30) are added. The solution is stirred then cooled in a cooling bath. When the temperature is about $-5°$ C., the catalyst (30 cc of ethanol KOH 2 N) is added. The addition must be very slow (about 1 hour) and the temperature must not exceed 0° C. Crystallization is noted in the reaction flask and develops with time; four hours after the beginning of the addition, the flask is refrigerated for the night.

The contents of the flask, which have partially solidified, are filtered. The crystals are rinsed with: 100, 100, and 200 cc of cold hexane then twice with 100 cc of cold methanol (to remove the KOH).
Yield: 94-95%
Melting point: 97%

Gas chromatography analysis indicates a 97% content of threo product and 3% of erythro product. There is no more starting product.

If desired, one can recrystallize in a solution of absolute alcohol containing 1% by weight of sulfuric acid to obtain a product having a 100% threo derivative content. In the absence of sulfuric acid, epimerization is observed, probably due to the KOH which has not been completely removed by the cold methanol.
Yield: 80%
Melting point: 100° C.

| Analysis: C$_{18}$H$_{17}$ON | C | H | N |
|---|---|---|---|
| Calc. % | 82.10 | 6.51 | 5.32 |
| Exp. | 82.04 | 6.53 | 5.39 |

Thin-layer chromatography: Adsorbent: Pfleuger Alumina (separates isomers).
Eluent: benzene
Developer: iodine
erythro: R$_f=0.8$; threo: R$_f=0.7$
Gas chromatography: Carlo Erba Fractovap Unit
Fluorosilicone (1.5%) column (2.50 m+⅛" inox) on Chromosorb
HMDS 80-100 mesh (98.5%); injection t°: 260° C.; column t°:
180° C. Carrier gas flow rate (N): 1.8 l/h; solvent: absolute alcohol.
Isomer retention time e: 28 min
Isomer retention time t: 35 min. Unless stated to the contrary, these will be the conditions for the other gas chromatographies.

Spectroscopy

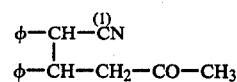

IR: $\nu C\!\equiv\!N$: 2220 cm$^{-1}$; $\nu C\!=\!O$: 1705 cm$^{-1}$
NMR:
$\delta = 7.17$ signal for 10 protons (phenyl)
$\delta = 4.10$ doublet for H$_{(1)}$$J_{H(1)H(2)}=7$ Hz (CDCl$_3$)
$\delta = 3.72$ multiplet for H$_{(2)}$
$\delta = 3.01$ multiplet for 2H$_{(3)}$
$\delta = 2.0$ singlet for CH$_3$ $_{(5)}$

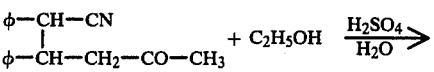

-continued $$\phi-CH-CO_2-C_2H_5$$
$$|$$
$$\phi-CH-CH_2-CO-CH_3$$
310

Yield: 80% gross
Yield of pure product: (gas chromatography) 65%

Thirty gms (0.114 mol) of crude 4-oxy, 2-diphenyl-pentane carbonitrile (98%t) are heated and dissolved in 270 cc alcohol with 95% LG. Ninety cc of conc. sulfuric acid are then poured in.

The solution is refluxed for 6 hours. Cooling is followed by extraction with 200, 100, 100, 100 cc of a 50:50 $CH_2Cl_2$/ether mixture until the aqueous phase has almost entirely lost its color. The recovered organic phase is rinsed twice with 100 cc of a 10% of $Na_2CO_3$ then 3 times with 100 cc of brine and finally dried on sodium sulfate.

After evaporating off the solvents, the substance is distilled in a vacuum. It is heated to 166°–167° C. (P=0.6 mm Hg); yield=approx. 80% (vitreous state). Gas chromatography indicates a 97% ester content. Recrystallization in absolute alcohol gives a product shown to be pure by gas chromatography.

Recrystallization: yield: 80% Melting point=95° C.

The melting point of the recrystallized product with a constant melting point (5 recrystallizations) is 110° C. (no difference in IR and gas chromatography with melting point 95° C.).

It should be noted that if one begins with 100% threo nitrile one obtains a product shown by gas chromatography to be practically pure after distillation.

| Analysis $C_{20}H_{22}O_3$ | C | H |
|---|---|---|
| Calc. % | 77.39 | 7.14 |
| Exp. | 77.14 | 7.12 |

Thin-layer chromatography: Adsorbent: silica (Merck pre-coated plastic plates)
Eluent: hexane/ethyl acetate 1:1
Developer: iodine $R_f$=0.4
Gas chromatography: The column and conditions are the same as for the analysis in stage 1.
Solvent: methyl-ethyl-ketone (ester retention time: 22 min)

Spectroscopy $$\phi-\overset{(4)}{CH}-\overset{(3)}{CO_2}-\overset{(2)}{CH_2}-\overset{(1)}{CH_3}$$
$$|$$
$$\phi-\overset{(5)}{CH}-\overset{(6)}{CH_2}-\overset{(7)}{CO}-\overset{(8)}{CH_3}$$

Melting point 110° C.
IR: $\nu C=O$ very large between 1700 and 1740 cm$^{-1}$; $>C=O$ and $CO_2C_2H_5$
NMR: $\delta$=7.30 signal for 10 aromatic protons (CDCl$_3$)
$\delta$=3.80 solid for 4 protons
$\delta$=2.45 solid for 2 protons
$\delta$=1.69 singlet for $CH_3(8)$
$\delta$=0.85 triplet for $CH_3(1)$ $J_{CH_3,CH_2}$=7 Hz Third Stage -continued $$\phi-CH-CO_2-C_2H_5$$
$$|$$
$$\phi-CH-CH_2-CO-CH_3$$
310

$\xrightarrow{NaOH}$ $$\phi-CH-CO_2Na$$
$$|$$
$$\phi-CH-CH_2-CO-CH_3$$
304

$\xrightarrow[H_2/Ni\ Raney]{P\ =\ 10\ bars\\ t\ =\ 100°\ C.}$ $$\phi-CH-CO_2Na$$
$$|$$
$$\phi-CH-CH_2-CHOH-CH_3$$

Thirty one g (0.10 mol) of the ethyl ester of 5-oxo-2, 3-diphenyl hexanoic acid are refluxed for 15 hours with constant stirring in 100 cc of soda N (exactly theoretical).

After cooling the solution is rinsed with 100 cc of ether to eliminate the unsaponifiables. After evaporating off the ether remaining in the water, the aqueous phase is placed in an autoclave. Raney nickel is then added with 50 cc of water. This nickel is obtained from 10 g of Raney alloy.

Hydrogenation is carried out at 100° C. at a pressure of 10 bars for 14 hours.

Stage four

After the hydrogenation operation, the nickel is separated by filtration, then the water is evaporated at low pressure. The residue (a white solid) is heated in 30 mol of demineralized water filtered when warm and cooled until it crystallizes. The yield (79%) is 24.2 g of very white crystals, melting point 297° C. Recrystallization is then carried out in alcohol with 95° GL.

Yield: 85% Melting point: 299°–300°

| Analysis: $C_{18}H_{19}O_3Na$ | C | H | N |
|---|---|---|---|
| calc. | 70.57 | 6.25 | 7.50 |
| Exp. | 70.66 | 6.29 | 7.70 |

Thin-layer chromatography shows a single spot:
Adsorbent: silica (Merck pre-coated plates)
Developer: U.V. and iodine
(a) Ethanol eluent: $R_f$=0.75
(b) Ethyl acetate eluent: $R_f$=0.30

Spectroscopy $$C_6H_5-\overset{(2)}{CH}-\overset{(1)}{CO_2Na}$$
$$|$$
$$\overset{OH}{|}$$
$$C_6H_5-\underset{(3)}{CH}-\underset{(4)}{CH_2}-\underset{(5)}{CH}-\underset{(6)}{CH_3}$$

Melting point: 298°–299° C.
IR: $\nu CO_2^{\ominus}$: 1370 and 1570 cm$^{-1}$; $\nu OH$: 3400 cm$^{-1}$ wide band.
NMR: $\delta$=7.0 signal for 10 aromatic protons (CD$_c$OD)
$\delta$=4.90 signal of OH
$\delta$=3.5 solid for $H_{(2)}$, $H_{(3)}$, $H_{(5)}$
$\delta$=2.10 doubled doublets (3 pics) for $CH_{2(4)}$ coupled with $H_{(3)}$ and $H_{(5)}$ J=7 Hz
$\delta$=1.2 doublet for $CH_3$ (6) for one isomer $J_{CH_3, H_{(5)}}$=6 Hz
$\delta$=1.05 doublet for $CH_3$ (6), for the other isomer $J_{CH_3, H_5}$=6 Hz Catalytic hydrogenation created a third center of asymetry. The NMR spectrum indicates ($\delta 1.05$, $CH_3$) the presence of two diastereoisomers in a ratio of 90:10.

EXAMPLE 5

Example of Preparation of the Lithium Salt of 5-Hydroxy-2,3-Diphenyl Hexanoic Acid For the first two stages one proceeds exactly as described in Example 4. In the third stage the soda is replaced by lithine LiOH in a stoichiometric quantity. The following crystals are obtained:

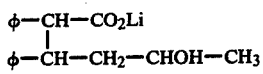

with a yield of about 75%
Melting point: 255° C.

| Analysis: $C_{18}H_{19}O_3Li$ | C | H | Li |
|---|---|---|---|
| Calculated %: | 74.48 | 6.60 | 2.39 |
| Experimental: | 74.40 | 6.44 | 2.20 |

Thin-layer chromatography shows a single spot:
Adborbent: silica (Merck pre-coated plates)
Developer: U.V. and iodine.
(a) Eluent ethanol with 95° LG: $R_f = 0.80$
(b) Eluent absolute ehtanol $R_f = 0.70$

Spectroscopy

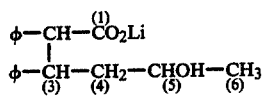

Melting point: 255° C.
IR: $\nu CO_2^\theta$: 1390 and 1550 $cm^{-1}$; $\nu OH = 3420$ $cm^{-1}$
NMR: $\delta = 6.9$ signals for 10 aromatic protons ($CD_3OD$)
$\delta = 4.95$ signal of OH
$\delta = 3.80$ solid for H (2), H (3), and H (5)
$\delta = 2.10$ doubled doublets (3 pics) for $CH_2$ (4) coupled with H (3) and H (5) J=7 Hz
$\delta = 1.15$ doublet for $CH_3$(6) one isomer $J_{CH_3,CH(5)} = 6$ Hz
$\delta = 1.05$ doublet for $CH_3$(6) the other isomer $J_{CH_3,H(5)} = 6$ Hz The proportions of the isomers are 90-10 t/e

PHARMACOLOGICAL RESULTS

All the experiments described below were carried out on male rats weighing between 170 and 220 g (Wistar AF strain) and male mice weighing between 18 and 23 g (Swiss NMRI strain), unless indicated to the contrary. All the experiments were conducted in a constant-temperature laboratory (22±1° C.). All the experiments were conducted with the double-blind technique (when the tests were carried out the experimenter did not know which animals had received the substance presumed to be active). Unless indicated to the contrary 10 animals per batch were always used.

Determination of Acute Toxicity in the Mouse

The $LD_{50}$ (determined by the Behrens and Karber method) of the sodium salt of 5-hydroxy-2, 3-diphenyl hexanoic acid (NaAHDH for short) administered orally was 998 mg/kg; intraperitoncally this $LD_{50}$ was 175 mg/kg.

Observation of Animals

With both the rat and the mouse, at doses less than the toxic doses (and beginning with 4 mg/kg orally or intraperitoncally), slight excitation was observed with enhanced reactivity to touch and sound stimuli. This stimulation was not accompanied by lack of motor coordination or abnormal or stereotyped movements. In addition, under these conditions, no change was observed in the diameter of the pupil but there was slight hyperthermia.

Only at doses very close to the lethal doses were trembling, hyperreactivity to very intense stimuli, interaggressivity, and convulsive phenomena extending to the rear paws observed. Under these conditions hyperthermia of about 2° C. was also observed.

In addition there was an increase of sexual behavior in the rat.

Motor Activity in the Mouse

The motor activity was determined with the aid of photoelectric cell actimeters (Boissier and Simon, Arch. int. Pharmacodyn. 1965, 158, 212-221). Twelve animals per batch were always used as a minimum.

Administered intraperitoneally immediately before the actimeter was switched on, NaAHDH at doses of 32 and 64 mg/kg causes an increase in motor activity in the mouse, significant for the first 30 minutes after the actimeter is attached. When the number of beams interrupted was observed every 5 minutes for the following 30 minutes, the increase was shown to be regular and constant up to the 60th minute after administration of NaAHDH (Table 1).

TABLE 1

| Time 0 NaAHDH mg/kg IP | 30 min | Test t | 30 + 5 min | 30 + 10 min | 30 + 15 min | 30 + 20 min | 30 + 25 min | 30 + 30 min | Test t |
|---|---|---|---|---|---|---|---|---|---|
| TIME | 393 ± 34 | — | 31 | 71 | 109 | 148 | 176 | 199 ± 36 | — |
| 16 | 376 ± 31 | — | 44 | 90 | 133 | 163 | 195 | 214 ± 28 | —* |
| 32 | 450 ± 39 | 1,540 | 65 | 118 | 183 | 242 | 285 | 325 ± 26 | 2,395 |
| 64 | 580 ± 47 | 3,311** | 90 | 195 | 297 | 396 | 429 | 558 ± 56 | 5,768** |

*significant difference at 0.05 threshold
**significant difference at 0.005 threshold

Motor Activity in the Rat

The motor activity was determined on male rats weighing between 90 and 110 g with the aid of the actimeter, the same instrument cited with regard to motor activity in the mouse.

The NaAHDH doses were given immediately before the actimeter was switched on.

The results are shown in Table 2. They show an increase in motor activity in the rat with 16 and 32 mg/kg interperitoneally and 32 and 64 mg/kg orally.

(b) Absence of Disturbance of Avoidance Conditioning

A simple conditioned-inhibition test was used,

TABLE 2

| NaAHDH mg/kg | Admin. | 30 min | Test t | NUMBER OF BEAMS INTERRUPTED ||||||| Test t |
|---|---|---|---|---|---|---|---|---|---|---|
| | | | | 30 + 5 min. | 30 + 10 min. | 30 + 15 min. | 30 + 20 min. | 30 + 25 min. | 30 + 30 min. | |
| 0 | ip | 407 ± 32 | | 11 | 20 | 26 | 33 | 38 | 50 ± 8 | |
| 16 | ip | 461 ± 32 | 1,100 | 39 | 67 | 104 | 133 | 156 | 182 ± 39 | 10,763 |
| 32 | ip | 631 ± 49 | 4,072 | 88 | 191 | 274 | 372 | 452 | 531 ± 84 | 8,377 |
| 0 | vo | 371 ± 20 | | 15 | 19 | 30 | 24 | 41 | 46 ± 14 | 2,717 |
| 32 | vo | 433 ± 43 | 1,554 | 31 | 69 | 100 | 118 | 131 | 164 ± 58 | 2,717 |
| 64 | vo | 517 ± 25 | 4,475 | 58 | 124 | 197 | 265 | 325 | 396 ± 62 | 7,633 |

*significant difference at 0.02 threshold
**significant difference at 0.001 threshold Perforated Board Test The technique and apparatus described by Boissier and Simon (Physiol. Behav. 1967, 2, 444–448) were used. In these experiments 15 animals per group were used (except for 30 for the controls and 30 for the 32 mg/kg dose). The results shown in Table 3 show a clear increase in movements which confirms the increase in motility observed with the actimeter and also a large increase in the holes explored, significant from a dose of 16 mg/kg of NaAHDH upward.

TABLE 3

| | PERCENTAGE OF CONTROLS ||
|---|---|---|
| NaAHDH mg/kg orally 60 min. before test | Holes explored in 5 min | Movements made in 5 min |
| 8 | 101 | 102 |
| 16 | 121 | 116 |
| 32 | 140 | 159 |
| 64 | 143 | 150 |

Hot Plate Test with the Mouse

This test was used to measure the reaction time of the animals to a painful stimulus. Ten animals were used per point. Fifteen minutes after oral administration of NaAHDH (32 mg/kg) the reaction time (licking of front paws) of the mice exposed to the hot plate was 5.8 seconds while that of the controls was 7.3 seconds (significant difference at the 0.05 threshold).

On the other hand, at the same dose NaAHDH did not increase or decrease the effects of an analgesic dose of morphine on this test.

Other Tests

These additional tests showed an absence of effect of NaAHDH. These effects are important inasfar as they enable the effectiveness profile of this substance to be delineated and compared to that of other known psychotropic substances. They are also important because they enable the absence of modification of a certain number of normal behaviors to be shown.

(a) Absence of Disturbance of Avoidance Conditioning

This avoidance conditioning in the rat placed in a two-compartment shuttle-box described by Boissier and Simon (Therapie 1968, 23, 1267–1276) was studied. In previously trained rats exhibiting a percentage of conditioned responses higher than 90%, NaAHDH at the dose of 16 and 64 mg/kg orally caused no change in the conditioning (study on 8 animals).

namely the four-plate test (Neuropharmacology, Aron et al, 1971, 10, 459–470). At doses of 4, 8, 16, 32, and 64 mg/kg (10 animals per group) no modification of conditioned inhibition was observed in the mouse. With this test, on the other hand, a slight in increase in the animals' performance was observed, but this seems to relate to the stimulating effect reported above.

(c) Absence of Modification of Hypnotic Effects

Administration of NaAHDH at doses of 16, 32, and 64 mg/kg orally at the same time as a barbiturate (pentobarbital) or 60 minutes before this hypnotic, caused no modification to the time taken to fall asleep or the length of sleep either in the mouse or in the rat.

(d) Absence of Effects on Classic Antidepressant Tests

1. Antireserpine Activity Test

At doses of 8, 16, and 32 mg/kg orally administered to rats and mice pretreated with reserpine (2.5 mg/kg IP 4 hours before NaAHDH), NaAHDH caused no modification of hyperthermia or drooping eyelid induced by reserpine.

2. Antioxotremorine Activity Test

In mice which received doses of 8, 16, and 32 mg/kg of NaAHDH orally or intraperitoneally the effects of oxotremorine (0.5 mg/kg IP) were unchanged, in terms of hyperthermia, trembling, lacrimation, hypersalivation, and defecation.

3. Anticataleptic Activity Test

With rats rendered cataleptic by administration of 8 mg/kg of prochlorperazine intraperitoneally, administration of NaAHDH (8 or 32 mg/kg intraperitoneally or orally) caused no modification to the cataleptic condition when tested by crossing the homolateral paws, the buddha test, or the rocking plate test.

4. Stereotypy test with Amphetamine

Administration of NaAHDH (32 or 64 mg/kg orally) 60 minutes before a dose of 2 mg/kg IP of amphetamine caused no modification in stereotyped movements caused by this substance in the rat.

(e) Absence of Inhibitory Effect of Monoaminoxidase

It has been found that at doses of 16 and 64 mg/kg orally, NaAHDH caused no potentialization of the effects of an infra-convulsant dose of tryptamine (3 mg/kg IV) in the rat.

(f) Absence of Interaction with Convulsants

In conjunction with an electric shock in the mouse, NaAHDH administered orally at doses of 4, 16 and 64 mg/kg 60 minutes before the electric shock modified neither the duration nor appearance of the convulsions and caused no increase in motility after the convulsion.

Administered at a dose of 64 mg/kg orally 30 minutes before a convulsant dose of cardiazol (160 mg/kg SC), NaAHDH caused no decrease in the latency of convulsions.

In conclusion, it emerges from the foregoing study that the effects of NaAHDH can be set forth as follows:

Increase of activity and wakefulness of the animals with no appearance of abnormal behavior, in particular of characteristic stereotyped movements; this increase was shown both in the rat and in the mouse by observation of the animals, measurements of motor activity, measurements of exploration of the perforated board, and decrease in the reaction time of the mice on a hot plate. The increase is clear (according to the tests) from doses between 16 and 32 mg/kg orally; it is exhibited rapidly after administration and persists for about 2 hours. These doses are far from the toxic doses ($ED_{50}/LD_{50}$ ratio about 15 in the mouse).

This increase in activity and wakefulness is not accompanied by disturbance of conditioned behaviors.

At clearly stimulating doses, NaAHDH causes no pentobarbital antagonism.

Absence of effect on the usual tricyclic antidepressant tests.

Absence of inhibitory effect of monoaminoxidase (tryptamine test).

Using the internationally accepted classification of Jean DELAY and Pierre DENIKER, this profile enables NaAHDH to be classified as a psychoanaleptic. Within this group of psychoanaleptics, NaAHDH can be clearly distinguished from the following categories:

nooanaleptic (for amphetaminic); by contrast to these drugs, NaAHDH causes no signs of sympathetic excitation, no antihypnotic effect, no stereotyped movements, and no antireserpine or anticataleptic action.

thymoanaleptics (or tricyclic antidepressants); by contrast with these substances, NaAHDH has a stimulating effect on normal animals but no effect on the antireserpine, antioxotremorine, or anticataleptic activity tests.

thymerethic (or monoaminoxidase inhibitors); by contrast with these substances, NaAHDH exhibits no activity with the antireserpine and anticataleptic action tests and does not potentialize stereotypy with amphetamine. In addition, NaAHDH does not potentialize the effects of tryptamine in the rat.

The observed effects thus makes NaAHDH belong to the psychostimulant group. The substance to which NaAHDH seems closest is caffeine. However, there are two important differences: NaAHDH has no antihypnotic effect while caffeine does, and NaAHDH does not potentialize apomorphine.

To summarize, NaAHDH behaves like a unique psychostimulant. Inasfar as predictive pharmacology can be applied to substances belonging to original chemical series (see SIMON and BOISSIER—*Confrontations psychiatriques* 1972, 9, 107–121) it can be predicted that NaAHDH will, in man, exercise a stimulating effect increasing wakefulness, which should permit therapeutic utilization in the following cases.

pediatrically: difficulties in concentration, apathy, asthenia, overwork, memory problems, difficulty in focusing attention;

with adults and geriatric patients: asthenia, decrease in mental activity, apathy, correction of sedation conditions caused by administration of antiepileptic drugs, tranquilizers, neuroleptics or others; apathy induced by Parkinson's disease.

It can also be predicted that the stimulating of NaAHDH has a favorable effect on patients with diminished libido and depressive conditions. This substance can be used by all routes of administration. The effective oral doses are from 80 to 1200 mg per day for the adult.

As a result of the foregoing, whatever the form of administration, the new drugs according to the invention have numerous advantages over previously known psychostimulants, in particular that of increased stimulating activity and virtually total absence of side effects.

It will be obvious to those skilled in the art that various changes may be made without departing from the scope of the invention and the invention is not to be considered limited to what is described in the specification.

What is claimed is:

1. A tetrahydro-α-pyrone of the formula:

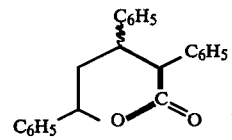

2. A compound of the formula

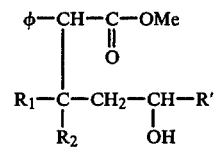

wherein $R_1$ is phenyl and $R_2$ is H; R' is alkyl of 1–4 carbon atoms, and Me is a pharmaceutically acceptable alkali metal.

3. An alkaline salt of 5-hydroxy 2,3 diphenyl hexanoic acid.

4. A compound in accordance with claim 2 of the formula

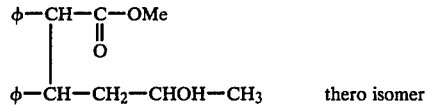

wherein Me is an alkali metal.

5. A compound in accordance with claim 4 wherein Me is Na.

6. A psychostimulant composition for increasing activity and wakefulness, comprising a psychostimulant effective amount of the compound of claim 4 and a pharmaceutically acceptable excipient.

7. A method of increasing activity and wakefulness comprising orally, parentally or rectally administering a psychostimulant - effective amount of the composition of claim 6 to a patient in need of said therapy.

* * * * *